United States Patent
Sauer et al.

[11] Patent Number: 5,901,196
[45] Date of Patent: May 4, 1999

[54] REDUCTION OF HITLIST SIZE IN SPIRAL CONE BEAM CT BY USE OF LOCAL RADON ORIGINS

[75] Inventors: Frank Sauer; Supun Samarasekera, both of Princeton; Kwok Tam, Edison, all of N.J.

[73] Assignee: Siemens Corporate Research, Inc., Princeton, N.J.

[21] Appl. No.: 08/940,489

[22] Filed: Sep. 30, 1997

[51] Int. Cl.$^6$ .................................................. A61B 6/03
[52] U.S. Cl. .................. 378/4; 378/15; 378/901
[58] Field of Search .................. 378/4, 15, 901

[56] References Cited

U.S. PATENT DOCUMENTS

| | | | |
|---|---|---|---|
| 5,257,183 | 10/1993 | Tam | 378/4 |
| 5,333,164 | 7/1994 | Tam | 378/8 |
| 5,383,119 | 1/1995 | Tam | 378/8 |
| 5,390,112 | 2/1995 | Tam | 378/17 |
| 5,446,776 | 8/1995 | Tam | 378/4 |
| 5,461,650 | 10/1995 | Tam | 378/4 |
| 5,463,666 | 10/1995 | Eberhard et al. | 378/4 |
| 5,748,697 | 5/1998 | Tam | 378/19 |
| 5,805,659 | 9/1998 | Tam | 378/15 |

*Primary Examiner*—David Vernon Bruce
*Attorney, Agent, or Firm*—Lawrence C. Edelman

[57] ABSTRACT

A method and apparatus for reconstructing an image of an object using a three dimensional (3D) computerized tomographic (CT) imager having a cone beam radiation source and detector arrangement for acquiring measurement data. The source and detector arrangement is operated at a plurality of source positions along a spiral scan path so as to acquire a corresponding plurality of sets of measurement data representative of radiation attenuation caused by the object. Image reconstruction processing information required for processing of the acquired measurement data in a Radon space partitioned by plurality of vertically oriented coaxial φ-planes for reconstructing the image, is pre-calculated and stored in a hitlist. The stored information is pre-calculated on less that all of the φ-planes, but due to a symmetry that is induced in the reconstruction processing, the stored information can be used for calculating Radon data for all of the φ-planes that partition the Radon space. The size of the hitlist is thus reduced by a factor equal to the number of φ-planes for which the stored information is re-used, e.g., 360 for ½ degree φ-plane spacing and storage of reconstruction processing information for a single φ-plane.

30 Claims, 4 Drawing Sheets

REDUCTION OF HITLIST SIZE IN SPIRAL CONE BEAM CT BY USE OF LOCAL RADON ORIGINS

BACKGROUND OF THE INVENTION

1. Field of the Invention

The present invention relates generally to computed tomographic (CT) imaging apparatus that performs three-dimensional (3D) image reconstruction by processing cone beam measurement data representative of an object, and more specifically, to a way of greatly reducing the size of a "hitlist" used to store pre-calculated information used in the reconstruction processing.

2. Description of the Background Art

Recently a system employing cone beam geometry has been developed for three-dimensional (3D) computed tomographic (CT) imaging that includes a cone beam x-ray source and a 2D area detector. An object to be imaged is scanned, preferably over a 360° angular range and along its length, by any one of various methods: i.e., by rotating the x-ray source in a scan path about the object while the object is being translated, by rotating and translating the source while the object remains stationary, or by rotating the object while one of the source or object is translated. These scanning techniques are all equivalent in that the position of the area detector is fixed relative to the source, and relative rotational and translational movement between the source and object provides the scanning (irradiation of the object by radiation energy). The cone beam approach for 3D CT has the potential to achieve 3D imaging in both medical and industrial applications with improved speed, as well as improved dose utilization when compared with conventional 3D CT apparatus (i.e., a stack of slices approach obtained using parallel or fan beam x-rays).

As a result of the relative movement of the cone beam source to a plurality of source positions (i.e., "views") along the scan path, the detector acquires a corresponding plurality of sets of cone beam projected measurement data (referred to hereinafter as measurement data), each set of measurement data being representative of x-ray attenuation caused by the object at a respective one of the source positions. After acquisition, the measurement data is processed for reconstructing a 3D image of the object.

As compared with the processing required for reconstructing an image when using an x-ray source supplying parallel or fan beams, the processing of the measurement data acquired when using a cone beam source is computationally much more complex. This is because when using a parallel or fan beam source, the measurement data is already directly representative of a 2D Radon transform of a cross-section of the object. However, this is not the case when using a cone beam source. Processing of the measurement data acquired using a cone beam source comprises:

1) conversion of the measurement data to Radon derivative data. This may be accomplished using the techniques described in U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993, hereby incorporated by reference, 2) conversion of the Radon derivative data to Radon data at polar grid points using, for example, the technique described in U.S. Pat. No. 5,446,776 entitled TOMOGRAPHY WITH GENERATION OF RADON DATA ON POLAR GRID POINTS issued Aug. 8, 1995, also hereby incorporated by reference, and 3) performing an inverse 3D Radon transformation of the Radon data using known techniques, such as those described in detail in the forenoted U.S. Pat. No. 5,257,183 for reconstructing image data that, when applied to a display, provides a view of the 3D CT image of the object.

Although the theory for exactly reconstructing an image using cone beam measurement data is generally known, such as from the US patents noted above, a practical implementation of the processing turns out to be quite problematic. Not only is the amount of measurement data to be processed very large and rapidly acquired in accordance with a timing that is mainly determined by the geometry of the scan path, but the calculations required on the acquired data are quite complex. For example, if one decides to reconstruct an object with $200\times200\times200=8\cdot10^6$ voxels (voxel=volume element of the object), for good quality one needs to obtain the object's 3-D Radon transform with a multiple amount (e.g., 4) of Radon samples, i.e., $32\cdot10^6$ samples, and then perform the Radon inversion. The most computationally expensive part of the object reconstruction is the calculation of the Radon derivative data (step 1 noted above). As noted in the above U.S. patents, as well as in detail in U.S. Pat. No. 5,463,666 entitled HELICAL AND CIRCLE SCAN REGION OF INTEREST COMPUTERIZED TOMOGRAPHY issued Oct. 31, 1995, hereby incorporated by reference, for calculating the value of the Radon data at a given Radon sample point, it is typically necessary to process the measurement data acquired from several source positions, with the measurement data from each source position developing a contribution to the final value for that sample point by way of data combination. Thus one needs to calculate about $100\cdot10^6$ line integral derivatives. Each line integral derivative requires the calculation of $200\cdot10^6$ single line integrals, since one uses the difference between two closely spaced line integrals to calculate a single line integral derivative. However, before one can perform these line integral derivative calculations, one has to compute for each Radon sample which source positions will provide the measurement data that must be processed, and determine the lines on the measurement data along which the integration must be performed. These latter determinations involve highly nonlinear calculations and are therefore computationally costly. In order to compute the contributing source positions, one has to intersect the source scanning path with the Radon integration plane as explained in the forenoted U.S. Pat. No. 5,463,666. When using a spiral scan path, this requires the solution of transcendental equations, which are computationally expensive. Furthermore, in addition to determining the lines on the measurement data along which the integration must be performed, one also has to calculate the appropriate end points of those lines for data combination purposes and region-of-interest masking. The complexity of these above-noted calculations leads to severe bottlenecks in processing of the measurement data, so as to prevent rapid and efficient image reconstruction.

In U.S. patent application 97E7969 application Ser. No. 08/940,924 entitled A PRE-CALCULATED HITLIST FOR REDUCING RUN-TIME PROCESSING OF AN EXACT CONE BEAM RECONSTRUCTION ALGORITHM, filed contemporaneously herewith, a method and apparatus is described in which before operation of a cone beam imaging apparatus for acquiring and processing of measurement data to reconstruct an image of an object, information required for processing of the acquired measurement data is pre-calculated and stored. The pre-calculated information is then used during the imaging operation of the cone beam apparatus for processing of the acquired measurement data to reconstruct an image of the object. The pre-calculated image reconstruction information is organized into what is referred to as a "hitlist". In general, the hitlist contains processing information that is determined primarily by geometric parameters of the imaging apparatus that are already predetermined during its imaging operation, such as the pitch and other parameters of the source/detector scan path, the object dimensions, the detector resolution, and a desired sampling of the scan path and the Radon space. The hitlist includes processing information indicating the correspondence between points in Radon space and the source positions that contribute thereto, parameters that define the line integrals that need to be calculated in the measurement data acquired at each of the source positions, as well as other information useful for image reconstruction processing.

Although calculation of the hitlist information is computationally expensive, since the information in the hitlist must be calculated anyway in order to process each set of the acquired measurement data during imaging operation of the apparatus, its pre-calculation provides a very significant speed-up of the run-time (image) processing of the measurement data and results in a greatly improved efficiency in the implementation of the image reconstruction algorithm. However, as described in more detail in the forenoted 97E7969 U.S. patent application, since hitlist information is required for each of the many points in Radon space that define the objects region of support, the size of the hitlist is actually quite large. For example, as previously noted, approximately $100 \times 10^6$ line integral derivative calculation are required. If the image reconstruction processing information stored in the hitlist comprises 24 bytes to describe the processing for determining each line integral, then 2.4 Gbytes of memory is required.

For practical reasons it would be desirable to reduce the memory requirement of the hitlist.

SUMMARY OF THE INVENTION

In accordance with the principles of the present invention, a symmetry is induced in the reconstruction processing so that the numerical values of the reconstruction processing information contained in the hitlist and calculated on less than all of a set of vertically oriented co-axial $\phi$-planes that partition the Radon space, is re-used for calculating Radon data for other ones of the $\phi$-planes that partition the Radon space. In a preferred embodiment, the hitlist only contains reconstruction processing information calculated on a single $\phi$-plane, e.g. for $(r_i, \theta_j, \phi=0°)$, which information is reused during the image reconstruction processing to determine the Radon data for all of the remaining $\phi$-planes. The size of the hitlist is thus reduced by a factor equal to the number of $\phi$-planes. For a Radon space sampling with $\Delta\phi=½°$ (i.e. 360 $\phi$-planes), this aspect of the invention allows the memory requirement for the hitlist to be reduced by a factor of 360. In accordance with a further aspect of the invention, a further symmetry is induced so as to enable an even further reduction of the size of the hitlist by a factor of 2, for a total reduction of 720. This reduction is significant, since an implementation of the hitlist in accordance with the prior art could easily consume several Gbytes of memory! Once the hitlist is of manageable size, one can be generous about the size of the individual information entries and include even more pre-calculated information for each entry, resulting in a further speed-up of the image reconstruction processing.

Hence, the invention reduces in a very significant way the memory requirement and processing time required for image reconstruction in accordance with an exact cone beam reconstruction algorithm.

Although, as to be described, use of a relative hitlist is based on a shift in the origin of the coordinate system of successive ones of the $\phi$-planes, since the origin shift in each $\phi$-plane is precisely known, it can be compensated for in the processing that follows. In accordance with a further aspect of the present invention, the origin shift is easily compensated for during the inversion processing of the 3-D Radon transform data.

DETAILED DESCRIPTION OF THE PREFERRED EMBODIMENTS

Figure 1:
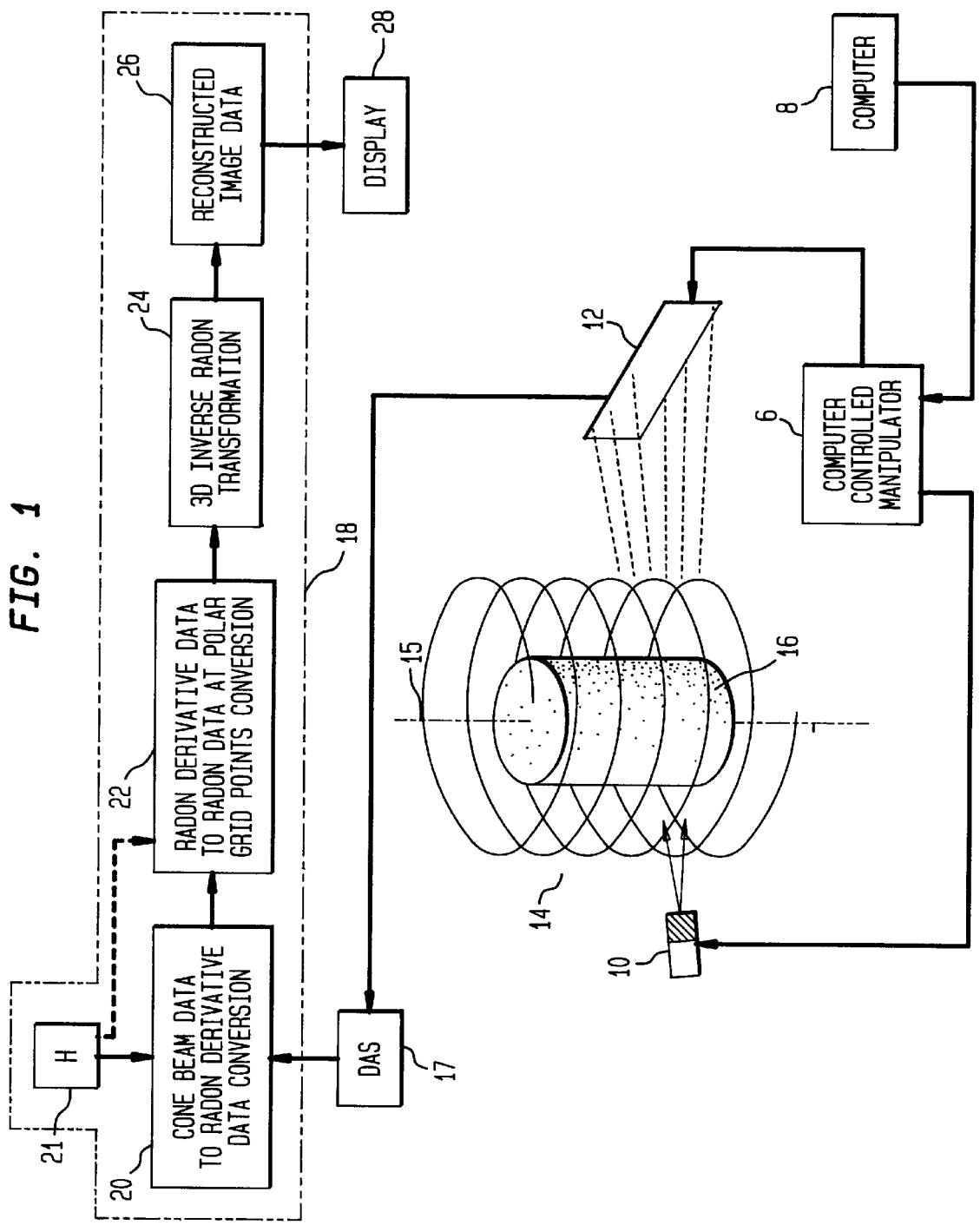
FIG. 1 is a block diagram and simplified perspective illustration of the imaging of an object using a cone beam imaging apparatus, wherein the apparatus uses a pre-calculated hitlist of reconstruction processing information for processing acquired measurement data in accordance with the principles of the present invention.

FIG. 1 illustrates a cone beam 3D CT imaging apparatus that operates in accordance with the principles of the present invention. Except as to be specifically described later with respect to implementation of image reconstruction processing in accordance with the present invention, the illustrated imaging apparatus is constructed and operates substantially the same as described in the forenoted U.S. Pat. Nos. 5,257,183 and 5,446,776.

Briefly, referring again to FIG. 1, a computer controlled manipulator 6, in response to control signals from an appropriately programmed computer 8, cause a source 10 of cone beam energy (such as x-rays) and a two-dimensional array detector 12 to cooperate (scan) at a plurality of discreet, sequentially occurring adjacent source positions, along a pre-defined source scanning path, illustrated as a spiral scan path 14 centered on a predetermined axis 15 of an object 16. As a result of the source/detector cooperation, detector 12 acquires complete cone beam measurement data which is then used for reconstructing an image of object 16. Alternatively, and equivalently, object 16 could be rotated and translated to cause scanning by a fixed position source and detector. Furthermore, the scanning can be accomplished in a continuous or stepwise manner, and the spiral path can have equally spaced turns (sometimes referred to as stages), or turns with decreasing pitch at the top and bottom edges of a region of interest of the object. Even furthermore, although source 10 is shown as an x-ray source, other types of imaging energy might be useful, such as neutrons, positrons, etc.

Computer 6, manipulator 8, source 10 and detector 12 cooperate to accomplish scanning of the object in a manner generally well understood by those skilled in this art, i.e., such as described in detail in the forenoted U.S. Pat. No. 5,463,666, and therefore discussion of further details of this portion of the operation of the cone beam imaging apparatus is deemed not necessary.

After the x-ray energy passes through the field of view of the imaging apparatus, measurement signals corresponding to the sensed x-ray energy falling on elements within detector 12 are supplied to a data acquisition system (DAS) 17 which, like the previously described portions of FIG. 1, may operate in a fashion well known to those of ordinary skill in this technology for digitizing, pre-processing, and storing of measurement data corresponding to the acquired measurement signals.

The cone beam measurement data from the DAS 17 is supplied to a buffer memory and image reconstruction processor 18, which may be a computer programmed to perform various data conversions that process the measurement data so as to reconstruct an image, generally illustrated by the blocks within processor 18. More specifically, at block 20 the measurement data is processed so as to be converted to Radon derivative data. A spherical coordinate system (r, θ, φ) is preferably used to facilitate the Radon inversion processing. This may be accomplished, in general, using the techniques described in the forenoted U.S. Pat. No. 5,257,183. However, as will be described in greater detail later, in accordance with the principles of the present invention, the speed and efficiency of this portion of the image reconstruction processing is improved by use of a "relative" hitlist ($H_r$) of pre-calculated image reconstruction processing information that is stored in a database 21, and used during run-time (imaging) operation of the apparatus for processing the acquired measurement data to reconstruct an image of the object.

Figure 5:
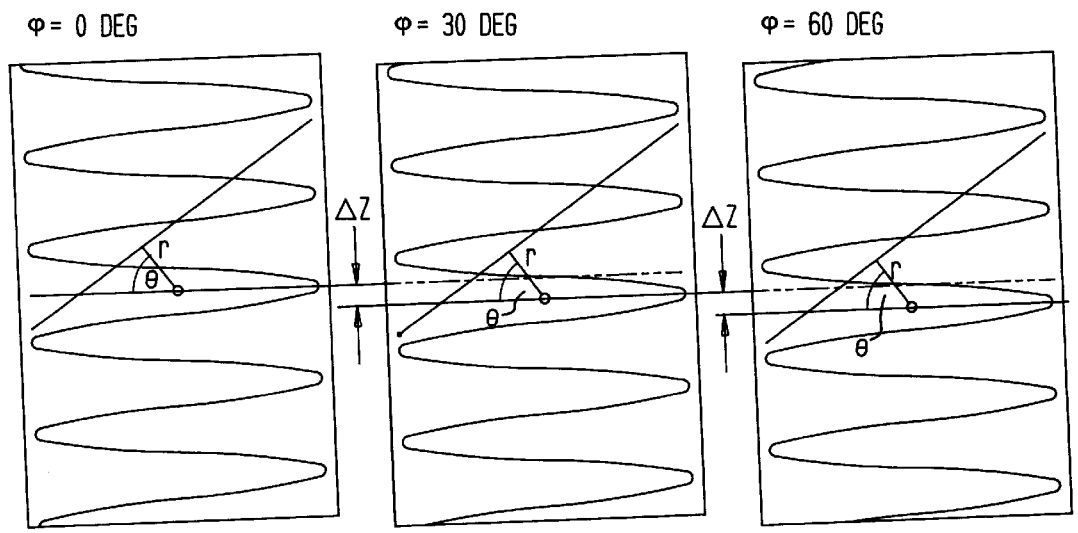
FIG. 5 illustrates use of local Radon origins for the successive $\phi$-planes of FIG. 4, for inducing a symmetry into the determinations illustrated therein, in accordance with one aspect of the present invention.

At block 22 the Radon derivative data is converted to Radon data at equally spaced polar grid points using, for example, the technique described in detail in conjunction with FIG. 5 of the forenoted U.S. Pat. No. 5,446,776. Briefly, as described therein, the Radon derivative data from block 20 is converted to Radon derivative data at equally spaced polar grid points using nearest neighbor or interpolation techniques, and then summed to develop the Radon data at equally spaced polar grid points. The hitlist of reconstruction processing information stored in database 21 preferably also provides pre-calculated information during this portion of the reconstruction processing, such as weighting information used for interpolation processing (as indicated by a dashed line from block 21 to block 22), thereby also improving the speed and efficiency of this portion of the reconstruction processing.

Figure 2:
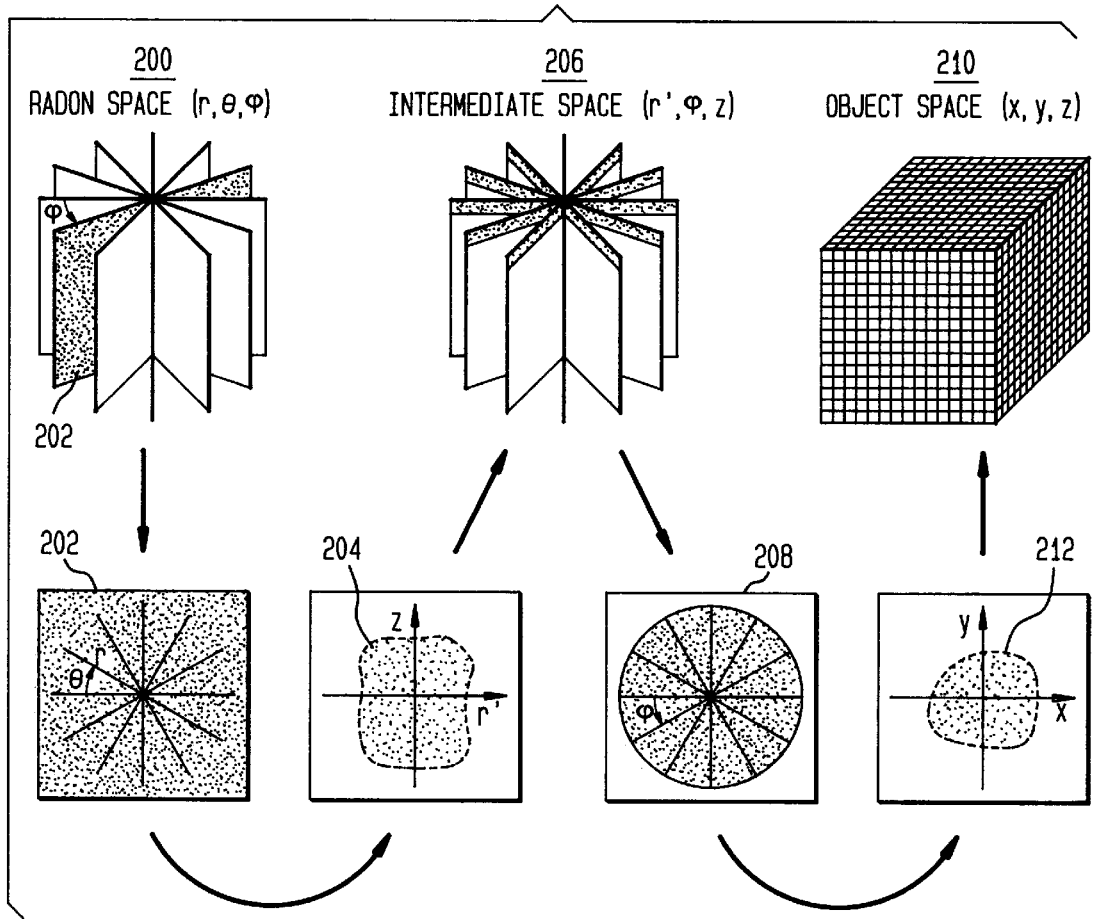
FIG. 2 illustrates 3D inverse transformation processing of 3D Radon data in accordance with an aspect of the present invention, for reconstructing an image of the object.

At block 24 the Radon data is subjected to inverse 3D Radon transformation processing. FIG. 2 generally illustrates one example of a two-step 3D Radon inversion procedure which is used in conjunction with the present invention. The two-step 3D Radon inversion processing of block 24, except for a slight modification which will be described later, is known and described, for example, in the forenoted U.S. Pat. No. 5,257,183. Briefly, one starts with the Radon data from block 22, sampled in a Radon space 200 that is defined by a spherical coordinate system (r, θ, φ), with one φ-plane 202 of a plurality of vertically oriented coaxial φ-planes being illustrated with a polar grid coordinate thereon. In the first reconstruction step, 2-D Radon inversions are performed on the Radon data in each of the φ-planes using a procedure such as filtered backprojection. Each φ-plane 202 will then contain a 2-D projection 204 of the object for the corresponding viewing angle, sampled in a Cartesian coordinate system (r',z). After the first 2D inversion, information about the whole object is contained in the cylindrical coordinate system 206 (r', φ, z). In the second reconstruction step, horizontal planes (z-slices) 208 parallel with the z axis are defined in system 206 and data descriptive of a 3D image of the object is developed in object space 210 slice-by-slice. More specifically, for each z-slice 208, a 2D CT reconstruction procedure, such as filtered backprojection, operates on the values of the 2D projection images in the plane of the z-slice, thereby calculating a 2D image 212 of the object for each z-slice. The final result is image data representative of the spatial distribution of the 3D object, sampled in the Cartesian coordinate system (x,y,z).

The image data developed thereby is stored at block 26 and then fed from reconstruction processor 18 to a display 28, which may operate in known fashion, to provide a 3D CT view of object 16.

Except for the determination and use of the relative hitlist, which is described next, a more detailed description of the blocks of FIG. 1 can be found in the forenoted patents incorporated by reference herein.

As previously noted, and as described in detail in the forenoted U.S. patent application 97E7969, before operation of a cone beam imaging apparatus for acquiring and processing of measurement data to reconstruct an image of an object, information required for processing of the acquired measurement data is pre-calculated and stored in database 21. The pre-calculated information is then used during the imaging operation of the cone beam apparatus for processing of the acquired measurement data to reconstruct an image of the object. The pre-calculated image reconstruction information is sometimes referred to as a "hitlist". In general, the hitlist contains processing information that is determined primarily by geometric parameters of the imaging apparatus that are predetermined during its imaging operation, such as the pitch and other parameters of the source/detector scan path, the dimensions of the object, the detector resolution, and a desired sampling of the scan path and the Radon space. The hitlist includes processing information indicating the correspondence between points in Radon space and the source positions that contribute thereto, parameters that define the line integrals that need to be calculated in the measurement data acquired at each of the source positions, as well as other information useful for image reconstruction processing.

Pre-calculation of the hitlist information provides a very significant speed-up of the run-time (image) processing of the measurement data and results in a greatly improved efficiency in the implementation of the image reconstruction algorithm. However, as described in more detail in the forenoted 97E7969 U.S. patent application, since hitlist information is required for determining data for each of the many points in Radon space that define the objects region of support, the size of the hitlist is actually quite large.

The present inventors have realized that a symmetry can be induced into the image reconstruction processing that determines the correspondence between points in Radon space and the source positions. As a result of such induced symmetry, hitlist information calculated for one of the φ-planes is also appropriate for processing measurement data to develop Radon data for other ones of the φ-planes. The manner of inducing this symmetry in the image reconstruction processing will be described in conjunction with FIG. 5.

Figure 3A:
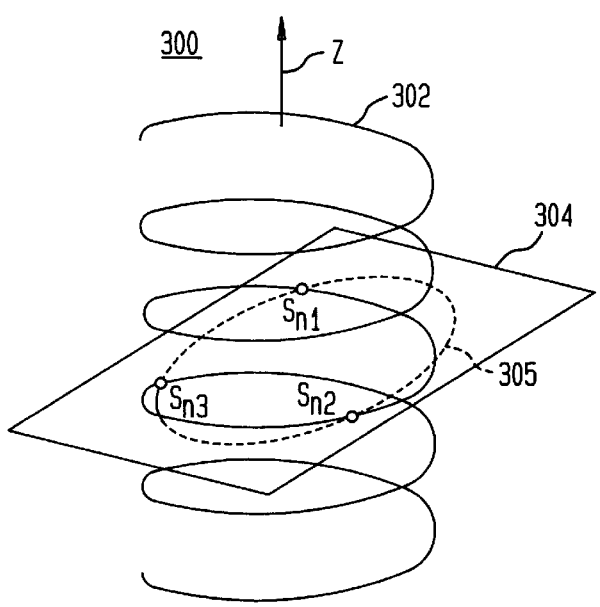
FIGS. 3a and 3b illustrate determination of the source positions which contribute to a given Radon sample point.
Figure 3B:
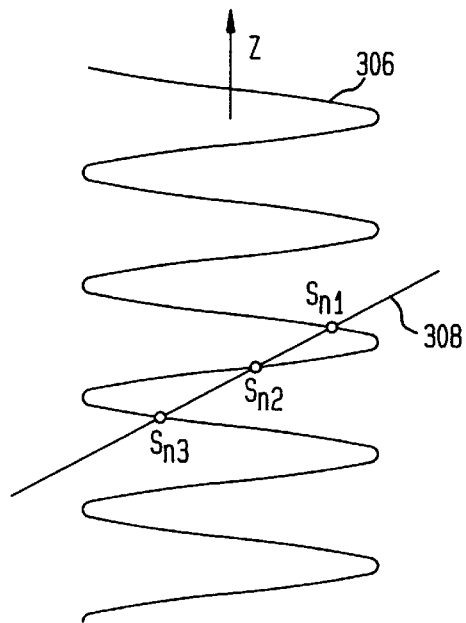
Figure 4:
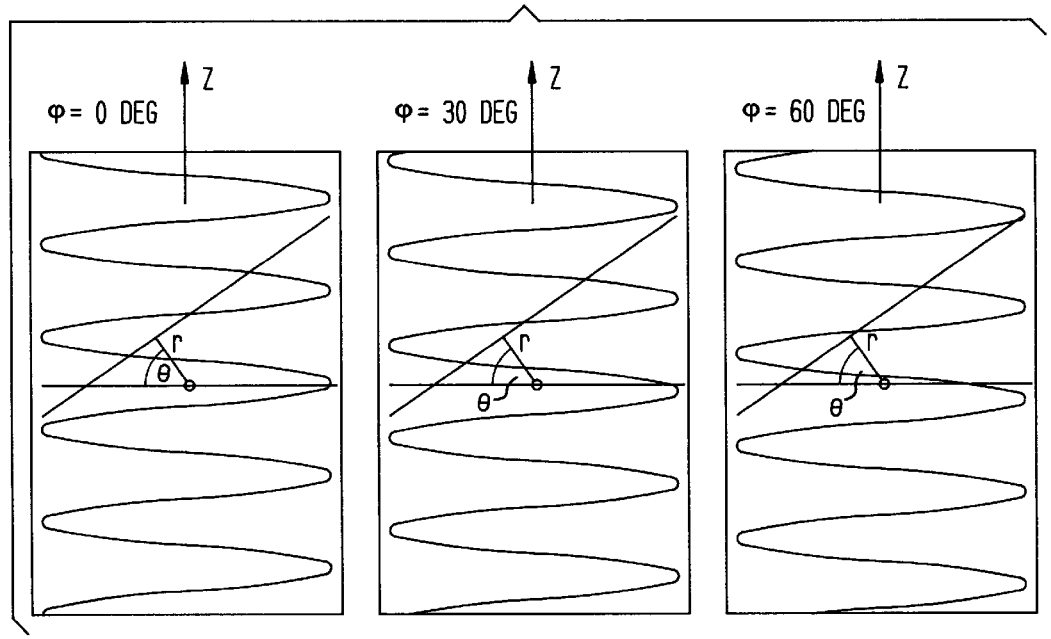
FIG. 4 illustrates determination of the source positions which contribute to a Radon sample point which is similarly positioned on selected ones of successive $\phi$-planes in Radon space.

However, before describing in detail how the symmetry is induced and can be exploited in accordance with various aspects of the invention, the reader is referred to FIGS. 3 and 4 for some additional background information. FIG. 3 illustrates determination of the source positions $S_{n1}$, $S_{n2}$ and $S_{n3}$ along scan path 302 which acquire measurement data to be processed for contributing to a given Radon sample point. As well known by those skilled in this art, 3D Radon transform datum at a given point (r, θ, φ) can be uniquely determined by the planar integral of the object's x-ray attenuation coefficient, with the integration plane determined by the vector (r, θ, φ), not specifically shown. The measurement data acquired by the detector at source positions which lie on the integration plane contribute to the particular Radon value. FIG. 3a depicts this situation in 3D. The illustrated exemplary integration plane 304 intersects the spiral scan path 302 at positions $S_{n1}$, $S_{n1}$ and $S_{n3}$. The intersections lie on an ellipse, shown by dashed line 305, which is generated by projecting the spiral in the z-axis direction onto integration plane 304. To calculate the source intersections, one merely projects both scan path 302 and integration plan 304 into the φ-plane (determined by the φ-coordinate of the Radon point), as shown in FIG. 3b. Then, one merely has to solve the 2-D problem of intersecting a sine-function 306 (projection of spiral 302) with a line 308 (projection of plane 304) to determine the position of points $S_{n1}$, $S_{n2}$ and $S_{n3}$. Finally, one translates these positions back into 3D space based on knowledge of the geometry of scan path 302. This procedure is repeated until source position information is developed for all the Radon points that are desired for reconstructing an image of the object with a desired resolution.

FIG. 4 illustrates determination of the source positions which contribute to Radon sample points which are similarly positioned on selected ones of successive φ-planes (0°, 30° and 60°) in Radon space, i.e., Radon sample points which have the same r and θ coordinates. As shown thereby, as we move from φ-plane to φ-plane while keeping r and θ constant, the spiral's projection shifts along the z-axis, which results in new intersections, related to the previous ones in a highly nonlinear way. When one stores these results in the hitlist, one needs separate, unique, entries for the Radon sample points of each φ-plane. For a more detailed description, the reader is referred to the forenoted U.S. Pat. No. 5,257,183 (FIGS. 3–10), or the forenoted U.S. patent application 97E7969.

The present inventors realized that although the position of the intersections of projections of the integration planes with the spiral scan path (i.e., contributing source positions) changed between the φ-planes in a highly nonlinear way, the shift of the spiral's projection along the z-axis changed in a very predictable, and in fact linear way. As shown by the three φ-planes illustrated in FIG. 4, the projection of the spiral scan path "shifts" in the z-axis direction with increases in the φ-plane index (e.g., from 0° to 30° to 60°). The present inventors take advantage of this predictability, as will be described below, in accordance with the principles of the present invention.

In accordance with one aspect of the invention, the hitlist entries calculated for the Radon sample points on one φ-plane can be used for the similarly positioned Radon sample points in other ones, and in fact all of the other ones, of the φ-planes. A visual illustration of the technique used by the present invention to achieve this result, is shown in FIG. 5. As shown therein, the Radon origin on each of successive ones of the φ-planes (with only φ-planes 0°, 30° and 60° being illustrated) is shifted by an amount (Δz) corresponding to the amount of z-axis shift that the projection of the spiral path 302 experiences between the successive φ-planes. The ΔZ illustrated in FIG. 4 corresponds to Δz times the number of φ-planes between 0° and 30°.

As a result of the origin shift for successive φ-planes, the intersections between the projections of the spiral and the integration plane are the same in the local coordinate systems of each φ-plane. Consequently, the same source positions, in a relative sense, contribute to a given r, θ Radon position independent of the φ-plane, and the reconstruction information in the hitlist intended for a given φ-plane can now be re-used for determining Radon data in any of the successive φ-planes. All that remains to be done is to make a compensation in the processing that follows to take the φ-plane origin shifts into account.

In accordance with a further aspect of the present invention, the two-step Radon inversion processing of block 24 of FIG. 1, is modified to allow one to establish on each of the φ-planes containing the Radon transform data, a local Radon origin, which local origin is independent of the local origin of each of the other ones of the φ-planes. Thus, the shifting of the local Radon origins of the Radon space φ-planes can be kept track of, and compensated for during Radon inversion processing.

More specifically, the compensation can be made during the first step of the Radon inversion processing shown in FIG. 2, by backprojecting the Radon data (from φ-planes) onto sample grids (z,r') which are not shifted, i.e., are offset, from the local Radon origins. Thus, the sample grids are already aligned in the z-axis direction and as such are part of a global grid. Consequently, the z-axis offset of the Radon origins is simply taken account of by introducing a corresponding z-axis delta into the coordinate variables during the Radon inversion backprojection. Alternatively, one can backproject onto z,r' grids which are shifted along with the local Radon origins, and then, before one performs the second step of the inversion processing (2D Radon inversion in the z-planes), shifting the backprojection results, i.e., images 204, a corresponding amount in the z-axis direction to compensate for the previous z-shift. This shifting can easily be accomplished using standard interpolation techniques.

What follows is a description of how to calculate the information included in "relative" hitlist 21, and how to extract information about all the φ-planes from it. First, it is necessary to introduce some nomenclature.

Nomenclature

The spiral scan path is defined in a cylindrical coordinate system, where the z-axis coincides with the axis of the spiral.

The Radon space is defined in regard to a spherical coordinate system for which the axis, around which the angle φ is measured, coincides with the z-axis of the cylindrical coordinate system.

The spiral scan path is sampled in equidistant φ-intervals with step size $\Delta\phi_{source}$. The sampled source positions along the scan path are denoted by $S_n$, n=0 ... $N_2$–1. The number of source positions $N_S$ depends on the length of the scan path and the sampling interval.

The φ-planes in Radon space are sampled in equidistant φ-intervals with step size $\Delta\phi_{Radon}$. The sampled φ-planes are denoted by $\phi_m$, m=0 ... M−1. The number of $\phi$-planes is given by M=$\pi/\Delta\phi_{Radon}$. The step size $\Delta\phi_{Radon}$ has to be chosen such that M is an integer. It is advantageous to make M an even integer, which we assume to be true in the following. We also make the assignments $\phi_0$=−$\pi/2$ and $\phi_{M-1}$=$\pi/2$−$\Delta\phi_{Radon}$, which leads to the correspondence $\phi_{M/2}$=0.

For the concept of local Radon origins to work in a straightforward way, we assume that $\Delta\phi_{source}$=$\Delta\phi_{Radon}$.

We use different Radon origins in the different $\phi$-planes. When we move from one $\phi$-plane to the next by the angular distance $\Delta\phi$=$\Delta\phi_{Radon}$, we translate the local Radon origin by $\Delta z$. The shift $\Delta z$ is determined by the pitch p of the spiral scan path and the angular sampling interval on the scan path $\Delta\phi$=$\Delta\phi_{source}$. The pitch p of the spiral is defined by how much the spiral path progresses in the z-direction during a full $2\pi$-turn. When we move from one source sample on the spiral to the next by $\Delta\phi(=\Delta\phi_{source}=\Delta\phi_{Radon})$, we move in the z-direction by $\Delta z = p \cdot \Delta\phi_{source}/2\pi$. Hence, by applying the same shift $\Delta z$ to the local origins of the $\phi$-planes in Radon space, we can, in regard to the local coordinate systems, make the projection of the spiral scan path look the same on every $\phi$-plane. This enables us to use the information in the relative hitlist for determining Radon data for all the $\phi$-planes.

Details of Hitlist Calculation

In order to calculate the hitlist information, we have to pick one particular $\phi$-plane in Radon space, which will be used to calculate information for the relative hitlist. We choose this plane to be the $\phi_{M/2}$-plane. We calculate how each sampled source position $S_n$ contributes to the $\phi_{M/2}$-plane, i.e. to all the sampled Radon positions $(r_i,\theta_j,\phi_{M/2})$ which lie in this plane. We go through all the sampled Radon positions $(r_i,\theta_j,\phi_{M/2})$ and calculate for each such Radon position the contributing source positions, as described above in conjunction with FIG. 3 (illustrating projecting both the spiral scan path and the integration plane corresponding to the Radon sample $(r_i,\theta_j,\phi_{M/2})$ into the $\phi_{M/2}$-plane.

Ideally, one would like to have measurements taken with the source being located at these exact intersections. As the scan path is sampled, however, one has to choose the actual source positions which come closest to the ideal positions. One can use either a nearest neighbor approach (picking the real source position which is closest to the ideal position) or an approach with interpolation (letting the two real source positions which are closest to the ideal position contribute in a weighted manner).

This Radon space driven hitlist is then re-sorted into the desired source space driven version, where the information is ordered source position by source position. The source driven version of the relative hitlist is stored for use during the image reconstruction processing of acquired measurement data, as previously described.

Details of Hitlist Structure

We refer to the information stored in the relative hitlist as $$I_n = \tilde{I}_{n,M/2}, n=0 \ldots N_I$$

The integer $N_I$ may be required to be larger than the number of source positions $N_S$, but it can also be smaller. The exact relationship between $N_I$ and $N_S$ depends on the relative size of the object in regard to parameters of the spiral scan path.

$\tilde{I}_{n/M/2}$ means that the particular information is for source position $S_n$ with regard to the $\phi_{M/2}$-plane in Radon space.

$\tilde{I}_{n/M/2}$ may have the following structure, containing a list of Radon positions (on the $\phi_{M/2}$-plane) to which source $S_n$ contributes, and the parameters specifying the corresponding integration lines:

| $I_n \equiv \tilde{I}_{n,M/2} =$ | |
|---|---|
| n, {Radon point #1, | Line parameters for point #1, |
| (e.g., indices i, j of Radon | (e.g., start and endpoint of an |
| sample position $r_i$, $\theta_j$) | integration line) |
| Radon point #2, | Line parameters for point #2, |
| Radon point #3, | Line parameters for point #3, |
| . . . | . . . } |

For a further understanding of how to use the relative hitlist, consider how the measurement data acquired from source position $S_n$ contribute to the $\phi_m$-planes for m≠M/2. With the local Radon origins shifted as described above, we have the following situation: the coordinates of source position $S_{n-1}$ with respect to the local coordinate system of the $\phi_{M/2}$-plane are the same as those of source position $S_n$ viewed from the local coordinate system of the $\phi_{M/2+1}$-plane. Hence, the measurement data from source position $S_n$ contributes to the Radon positions in the $\phi_{M/2+1}$-plane just like the measurement data from source position $S_{n-1}$ contributes to the Radon positions in the $\phi_{M/2}$-plane. The corresponding information is stored in $I_{n-1}$. This holds true if indices n and m increase in the same direction. If index n increases in the direction in which m decreases, measurement data from source position $S_{n+1}$ contributes to the Radon positions in the $\phi_{M/2}$-plane just like the measurement data from source position $S_n$ contributes to the Radon positions in the $\phi_{M/2+1}$-plane.

In general, if $I_{n,m}$ denotes the image reconstruction information for processing the measurement data from source position $S_n$ for developing contributions to the Radon positions in the $\phi_m$-plane, the following general relationship holds:

i.e. we find the information $\tilde{I}_{n,m}$ in the relative hitlist by $$\tilde{I}_{n,m} = \tilde{I}_{n \pm \Delta m, M/2} = I_{n \pm \Delta m} \text{ with } \Delta m = M/2-m,$$

looking up how source $S_{n \pm \Delta m}$ contributes to the $\phi_{M/2}$-plane. Again, the plus sign applies if indices n and m increase in the same direction, the minus sign, if index n increases in the direction that m decreases.

Assuming as before that M is an even integer, there are M values of $\Delta m$ in the range −M/2, −M/2+1, . . . , M/2−2, M/2−1. Hence, for processing the measurement data acquired at a given source position $S_n$, one needs to look at the relative hitlist information $$I_{n \pm (-M/2)}, I_{n \pm (-M/2+1)}, I_{n \pm (M/2-2)}, I_{n \pm (M/2-1)}$$

in order to know how that measurement data contributes to the Radon positions in each of the $\phi$-planes.

Figure 6A:
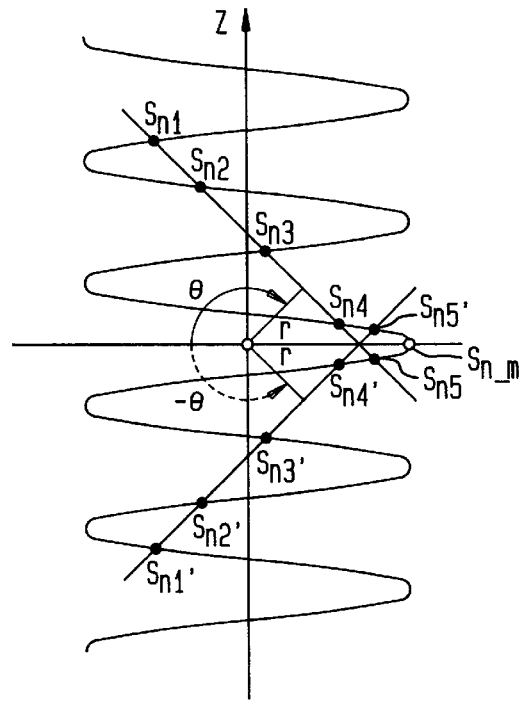
FIGS. 6a and 6b illustrate a further aspect of the invention wherein an additional symmetry in the scan path/integration plane intersection is exploited to enable an even further reduction in the size of the hitlist.
Figure 6B:
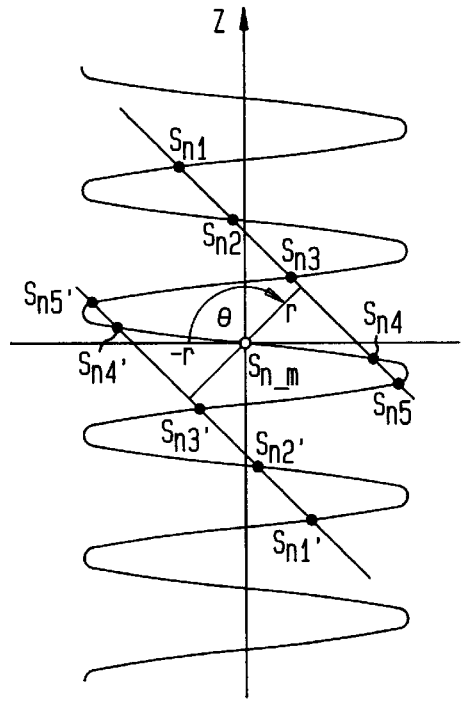

FIGS. 6a and 6b illustrate a further aspect of the invention wherein an additional symmetry in the scan path/integration plane intersections is induced and exploited to enable an even further reduction in the size of the hitlist. As shown thereby, the projection of the spiral source sampling path onto a $\phi$-plane is a sine-function along the z-axis, having a certain phase shift. One can adjust the z-axis of the Radon origin of the $\phi$-plane coordinates such that the sine-function phase shift is 0 or $\pi$ (sin or −sin), or such that the phase shift is $\pi/2$ or −$\pi/2$ (cos or −cos). In the cos-case (FIG. 6a), the projected spiral appears symmetric in regard to the z-coordinate of the local Radon origin, and in the sin-case (FIG. 6b), it appears antisymmetric with respect to the local Radon origin. In either case, if we sample the spiral scan path in a way that the positions of groups of the samples (such as $S_{n1}$ to $S_{n5}$ as compared with $S_{n_1'}$ to $S_{n_5'}$) have the same symmetry as the scan path itself, we can exploit such symmetry to reduce the size of the relative hitlist by an additional factor of two. For example, due to this added symmetry, hitlist information relating to sample $S_{n1}$ can be re-used for sample $S_{n1'}$.

Figure 7:
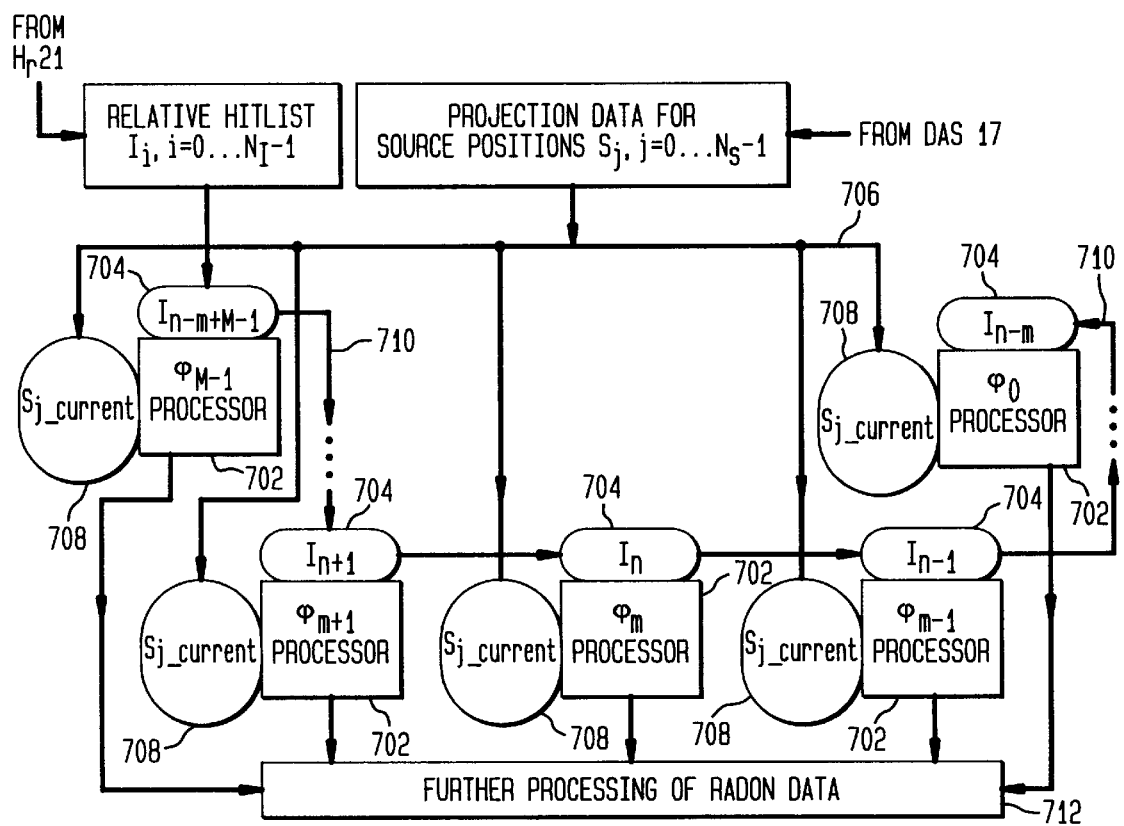
FIG. 7 illustrates a multiprocessor implementation for the processing of cone beam measurement data as shown in FIG. 1, in accordance with a further aspect of the present invention.

FIG. 7 illustrates an efficient multiprocessor implementation for the processing of cone beam measurement data as shown in block 20 of FIG. 1, in accordance with a further aspect of the present invention. During runtime (image operation of the apparatus), we receive the measurement data (which may be pre-processed: normalized, scaled, corrected for detector non-uniformities, etc). Using the relative hitlist, we then perform line integral calculation on the measurement data in order to calculate the Radon data of the object. A speed-up of the Radon data calculations is achieved by a multiprocessor hardware arrangement for parallel processing As shown in FIG. 7, the arrangement assigns different processors 702 to different φ-planes in Radon space. Measurement data ($S_j$) are broadcast to local memories 704 associated with each of φ-plane processors 702 via a global broadcast bus 706. Hitlist data ($I_r$) are propagated to local memories 708 also associated with each of φ-plane processors 702 via local interconnects 710 in a pipeline fashion. The calculated Radon data are stored in further local memories (not shown) of φ-plane processors 702 for further processing 712 in accordance with the prior art. This architecture keeps the amount of necessary data traffic low and, furthermore, handles it efficiently.

More specifically, the number of processors $N_P$ of the multiprocessor system is equal to the number of φ-planes in Radon space divided by an integer q. Each processor handles one particular φ-plane (as shown in FIG. 7, q=1), or a fixed set of q φ-planes. The measurement data are broadcast to all of processors 702 (equivalently, they are contained in a shared memory location to which all the processors have access). In operation φ-plane processors 702 obtain and store local copies of the measurement data. Each φ-plane processor 702 stores the hitlist information which is relevant for its current task (processing the data from source $S_n$ for contribution to the Radon data of a fixed set of φ-planes) in its own, local memory. The relative hitlist data are fed into the multiprocessor system in a pipeline fashion. After the data from source $S_n$ are processed, the hitlist information moves "downstream" such that every φ-plane processor 702 has now available in its local memory the information which is relevant for processing the measurement data from the next source position $S_{n+1}$.

Thus, there has been shown and described a novel method and apparatus for greatly reducing the size of the image reconstruction hitlist, thereby speeding-up and improving the efficiency of the image reconstruction processing in a cone beam 3D CT imaging apparatus. Many changes, modifications, variations and other uses and applications of the subject invention will, however, become apparent to those skilled in the art after considering this specification and its accompanying drawings, which disclose preferred embodiments thereof. For example, information in addition to that already described could be stored in the hitlist for later use, and the stored information could be sorted in ways different from that already described, for further facilitating the image reconstruction processing. Additionally, although a database 21 is described for sorted in ways different from that already described, for further facilitating the image reconstruction processing. Additionally, although a database 21 is described for storing the hitlist information, other types or arrangements of data storage could be used. Furthermore, although in the illustrated embodiment we assumed that $\Delta \phi_{source} = \Delta \phi_{Radon}$. This can be generalized such that $\Delta \phi_{source} = n \Delta \phi_{Radon}$, where n is an integer. For this alternative, one would calculate the hitlist information on n successive φ-planes and store it. The case $\Delta \phi_{Radon} = n \Delta \phi_{source}$ for integer n works without any modification to the described n=1 case. In general, use of the relative hitlist is based on the general symmetry $$I_{\phi source, \phi Radon} = I_{\phi source + \Delta\phi, \phi Radon - \Delta\phi}.$$

All such changes, modifications, variations and other uses and applications which do not depart from the general teaching of the invention herein, are deemed to be covered by this patent, which is limited only by the claims which follow as interpreted in light of the foregoing description.

What is claimed is:

1. A method of operating a 3D CT imaging apparatus having a cone beam radiation source and detector arrangement, for reconstructing an image of an object that is scanned by said source and detector arrangement, comprising the following steps:

operating said source and detector arrangement at a plurality of source positions along a spiral scan path so as to acquire a corresponding plurality of sets of measurement data representative of radiation attenuation caused by said object, and processing the acquired measurement data using pre-calculated and stored image reconstruction processing information that was calculated on less that all of a plurality of vertically oriented coaxial φ-planes that partition Radon space, for developing numerical values for Radon data samples on all of said φ-planes that partition the Radon space.

2. The method of claim 1, wherein said processing step comprises, using pre-calculated image reconstruction processing information calculated on a single φ-plane, for determining a numerical value for the Radon data samples for all of the φ-planes.

3. The method of claim 1, wherein said processing step comprises, inducing a symmetry into the image reconstruction processing of the measurement data so that a correspondence is developed between the relative source positions and Radon data samples over a plurality of φ-planes.

4. The method of claim 3, wherein said inducing step comprises establishing on each of successive ones of the φ-planes a local Radon origin, which Radon origins are independent of each other.

5. The method of claim 4, wherein said establishing step comprises, shifting the Radon origin for each of successive ones of said φ-planes an amount corresponding to an amount of z-axis shift that a projection of the spiral scan path experiences between the successive φ-planes.

6. The method of claim 4, including a further processing step of performing two-step Radon inversion processing of the Radon data to develop image reconstruction data in a coordinate system having a global origin, wherein the shift of the local Radon origins of the φ-planes are compensated for during the Radon inversion processing.

7. The method of claim 6, wherein said two-step Radon inversion processing includes a first step for backprojecting the Radon data for each of said successive φ-planes to make 2D images on grids (z,r') of φ-planes having local origins which are already part of a global grid, the z-axis shift of the Radon origin for each of said successive φ-planes that are input to the Radon inversion processing being taken into account by introducing a Δz offset into the coordinate variables of the backprojecting processing that corresponds to the amount of z-axis shift of the Radon origin of each of the φ-planes.

8. The method of claim 6, wherein said two-step Radon inversion processing includes a first step for backprojecting the Radon data for each of said successive φ-planes to make 2D images on grids (z,r') of φ-planes having local origins which are shifted along with the local Radon origins of the φ-planes that are input to the Radon inversion processing, and then, before one performs a second step of the two-step inversion processing, shifting in the z-axis direction the backprojection results from the first step, in order to compensate for the previous z-shift of the local origins.

9. The method of claim 8, wherein said shifting of the backprojection results comprises interpolating new image values that are shifted in the z-axis direction from 2d images that resulted from the first backprojection step.

10. The method of claim 1, wherein said processing step comprises,
    organizing the pre-calculated image reconstruction processing information into a database.

11. The method of claim 10, wherein said processing step comprises,
    organizing the pre-calculated image reconstruction processing information into a database sortable by sample points in Radon space, so that less than all of the maximum samples of Radon data will be determined, thereby reconstructing the image in a desired resolution that is less than a maximum resolution.

12. A method of operating a 3D CT imaging apparatus having a cone beam radiation source and detector arrangement, for reconstructing an image of an object that is scanned by said source and detector arrangement, comprising the following steps:
    before the acquisition of measurement data during an imaging operation of the apparatus,
    pre-calculating and storing image reconstruction processing information required for processing of the acquired measurement data in Radon space partitioned by a set of vertically oriented co-axial φ-planes to develop contributions to the final reconstruction of the image, which information is calculated on less than all of said φ-planes; and
    during the imaging operation of the apparatus,
    operating said source and detector arrangement at a plurality of source positions along a scan path so as to acquire a corresponding plurality of sets of said measurement data, and
    processing the acquired measurement data using said pre-calculated image reconstruction processing information on said single φ-plane in a relative way to determine Radon data for other ones of the φ-planes and reconstructing the image.

13. The method of claim 12, wherein said processing step comprises,
    inducing a symmetry into the image reconstruction processing of the measurement data so that a correspondence is developed between the relative source positions and Radon data samples over a plurality of φ-planes.

14. The method of claim 13, wherein said inducing step comprises establishing on each of successive ones of the φ-planes a local Radon origin, which Radon origins are independent of each other.

15. The method of claim 14, wherein said establishing step comprises,
    shifting the Radon origin for each of successive ones of said φ-planes an amount corresponding to an amount of z-axis shift that a projection of a spiral scan path experiences between the successive φ-planes.

16. The method of claim 14, including a further processing step of performing two-step Radon inversion processing of the Radon data to develop image reconstruction data in a coordinate system having a global origin, wherein the shift of the local Radon origins of the φ-planes that are input to the Radon inversion processing are compensated for during the Radon inversion processing.

17. The method of claim 16, wherein said two-step Radon inversion processing includes a first step for backprojecting the Radon data for each of said successive φ-planes to make 2D images on grids (z,r') of φ-planes having local origins which are already part of a global grid, the z-axis shift of the Radon origin for each of said successive φ-planes that are input to the Radon inversion processing being taken into account by introducing a Δz offset into the coordinate variables of the backprojecting processing that corresponds to the amount of z-axis shift of the Radon origin of each of the φ-planes.

18. The method of claim 16, wherein said two-step Radon inversion processing includes a first step for backprojecting the Radon data for each of said successive φ-planes to make 2D images on grids (z,r') of φ-planes having local origins which are shifted along with the local Radon origins of the φ-planes that are input to the Radon inversion processing, and then, before one performs a second step of the two-step inversion processing, shifting in the z-axis direction the backprojection results from the first step, in order to compensate for the previous z-shift of the local origins.

19. The method of claim 18, wherein said shifting of the backprojection results comprises interpolating new image values that are shifted in the z-axis-direction from 2D images that resulted from the first backprojection step.

20. The method of claim 12, wherein said processing step includes the further step of,
    inducing a symmetry into the image reconstruction processing of the measurement data so that a spatial correspondence is developed between the position of samples on either side of a local origin in a projection of a spiral scan path onto a φ-plane.

21. The method of claim 12, wherein said pre-calculating and storing step comprises,
    calculating as said image reconstruction processing information which is determined by pre-determined geometric parameters of the scan path and the detector, and a desired sampling of the scan path and Radon space.

22. The method of claim 12, wherein said pre-calculating and storing step comprises,
    organizing the pre-calculated image reconstruction processing information into a database.

23. The method of claim 22, wherein said organizing step comprises,
    organizing the pre-calculated image reconstruction processing information into a database sortable by sample points in Radon space, so that less than all of the maximum samples of Radon data will be determined, thereby reconstructing the image in a desired resolution that is less than a maximum resolution.

24. The method of claim 12, wherein said pre-calculating and storing step comprises,
calculating as said image reconstruction processing information that information which calculates Radon data on a single given φ-plane.

25. The method of claim 24, wherein said processing step comprises using the information calculated on said single given φ-plane to determine Radon data for all of the remaining φ-planes.

26. A scanning and data acquisition apparatus for three dimensional (3D) computerized tomography (CT) imaging of an object in a field of view radially centered on a predetermined axis, comprising:
an energy source (10) for emitting energy in the form of a cone beam;
an area detector (12) for detecting as measurement data cone beam energy after attenuation by passage through an object to be imaged;
a manipulator (6) for movably positioning said source and detector along a scan path relative to the object, to cause irradiation of said object by said source at multiple source positions along said scan path about said object, said detector acquiring a corresponding set of measurement data at each said source position;
control means (8) for defining the scan path as a plurality of spaced stages on a predetermined geometric surface surrounding the field of view, with each of a plurality of planes that pass through the field of view and intersect the scan path in at least one point as well as the area detector, being useful for calculating Radon data at a given one of a plurality of Radon sample points that sample a Radon space partitioned by a set of vertically oriented co-axial φ-planes;
image reconstruction processing means (18) including means for calculating Radon data for each of said Radon sample points by processing multiple ones of the sets of measurement data, for developing image data; and
display means (28) responsive to said image data for displaying a reconstructed image of the object;
wherein said image reconstruction processing means (18) includes a database (21) of reconstruction processing information that is calculated on less than all of said φ-planes, which information is pre-calculated and stored before acquisition of the measurement data, and then used by said image reconstruction processing means (18) during imaging operation of said apparatus for facilitating processing of the measurement data to calculate the Radon data for all of the φ-planes.

27. Apparatus in accordance with claim 26, wherein said image reconstruction processing means (18) includes Radon derivative calculating means (20) responsive to the image reconstruction processing information stored in said database (21) for calculating Radon derivative data for each of said Radon sample points in Radon space by processing line integral values from multiple ones of the sets of measurement data.

28. Apparatus in accordance with claim 27, wherein said image reconstruction processing means (18) includes Radon derivative data converting means (22) responsive to the image reconstruction processing information stored in said database (21) and said Radon derivative data for calculating Radon data at equally spaced polar grid points.

29. Apparatus in accordance with claim 27, wherein said image reconstruction processing means (18) includes inverse transformation processing means (24) responsive to said Radon data at equally spaced polar grid points for performing a 3D inverse Radon transformation of said Radon data to develop said image data.

30. Apparatus in accordance with claim 26, wherein said image reconstruction processing means (18) includes a two-step Radon inversion processor (24) which independently processes each of said φ-planes of Radon data, for developing said image data.

* * * * *